(12) United States Patent
Pappas et al.

(10) Patent No.: US 12,394,519 B2
(45) Date of Patent: Aug. 19, 2025

(54) SYSTEM AND METHOD FOR GENERATING BRAIN DATA VISUALIZATIONS BASED ON FEDERATED ANALYSIS OF BRAIN DATA IN A COMPLEX COMPUTING NETWORK

(71) Applicant: Alzheimer's Association, Chicago, IL (US)

(72) Inventors: Ioannis Pappas, Los Angeles, CA (US); Arthur W. Toga, Los Angeles, CA (US); Heather Snyder, Chicago, IL (US); Maria Carrillo, Chicago, IL (US); Ryan Cabeen, Los Angeles, CA (US); Scott Neu, Santa Monica, CA (US)

(73) Assignee: Alzheimer's Association, Chicago, IL (US)

( * ) Notice: Subject to any disclaimer, the term of this patent is extended or adjusted under 35 U.S.C. 154(b) by 391 days.

(21) Appl. No.: 17/973,948

(22) Filed: Oct. 26, 2022

(65) Prior Publication Data

US 2023/0126589 A1    Apr. 27, 2023

Related U.S. Application Data

(60) Provisional application No. 63/272,249, filed on Oct. 27, 2021.

(51) Int. Cl.
*G16H 40/60*    (2018.01)
*A61B 5/00*    (2006.01)

(52) U.S. Cl.
CPC .......... *G16H 40/60* (2018.01); *A61B 5/0022* (2013.01)

(58) Field of Classification Search
CPC .............................. G26H 40/60; A61B 5/0022
(Continued)

(56) References Cited

U.S. PATENT DOCUMENTS 6,397,224 B1 * 5/2002 Zubeldia ................ G16H 10/60
707/999.102
7,191,463 B2 * 3/2007 Dick ..................... G06F 21/6245
726/4

(Continued)

FOREIGN PATENT DOCUMENTS

WO    WO-0142883 A2 *  6/2001    ........... G06F 19/322
WO    WO-2014194406 A1 * 12/2014    ............. G06F 16/00

OTHER PUBLICATIONS

International Preliminary Report on Patentability dated Apr. 30, 2024, in connection with PCT/US2022/047843, 4 pages.

(Continued)

*Primary Examiner* — Michael Tomaszewski
(74) *Attorney, Agent, or Firm* — Baker & McKenzie LLP

(57) ABSTRACT

The disclosed systems relate to generating brain data visualizations based on federated analysis of brain data. In exemplary embodiments, the brain data visualizations are generated using a system comprising a framework. The framework may include a first computing platform that comprises one or more servers. The framework may also include a first application for communicating via a communication network with a second computing platform that is different from the first computing platform. The second computing platform may comprise a database that stores protected medical data including a plurality of data elements that are directly inaccessible individually or directly inaccessible in aggregate by a user of the first computing platform. In one embodiment, the one or more servers of the first computing platform comprise memory storing instructions that are executable by one or more computer processors of the first computing platform to execute the various processing stages outlined in this disclosure.

20 Claims, 8 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 8,682,049 | B2* | 3/2014 | Zhao .................... | G06Q 10/103 |
| | | | | 382/128 |
| 10,204,117 | B2* | 2/2019 | Chau ....................... | G06F 16/51 |
| 10,331,852 | B2* | 6/2019 | Dormer ................. | G16H 40/67 |
| 10,452,812 | B2* | 10/2019 | Gogin ................. | G06F 21/6254 |
| 10,474,640 | B1* | 11/2019 | Roche, Jr. ............... | H04L 67/06 |
| 10,878,361 | B2* | 12/2020 | Tanwir ................. | G06F 3/0481 |
| 11,145,404 | B1* | 10/2021 | Sin Kwok Wong ......................... | |
| | | | | G06F 9/45558 |
| 11,688,495 | B2* | 6/2023 | De Francesco ........ | G16H 10/60 |
| | | | | 713/182 |
| 12,272,435 | B2* | 4/2025 | De Francesco ........ | G16H 10/60 |
| 2003/0140043 | A1* | 7/2003 | Hotchkiss .............. | G16H 10/20 |
| 2003/0215092 | A1* | 11/2003 | Dick ....................... | G16H 80/00 |
| | | | | 380/246 |
| 2005/0027564 | A1* | 2/2005 | Yantis ..................... | G16Z 99/00 |
| | | | | 705/2 |
| 2005/0097123 | A1* | 5/2005 | Baek ...................... | G16H 70/60 |
| | | | | 707/999.102 |
| 2008/0021730 | A1* | 1/2008 | Holla .................... | G16H 80/00 |
| | | | | 705/2 |
| 2008/0082966 | A1* | 4/2008 | Dorn ...................... | G06F 9/545 |
| | | | | 717/120 |
| 2011/0218820 | A1* | 9/2011 | Himes .................... | G16H 20/70 |
| | | | | 705/3 |
| 2014/0114672 | A1* | 4/2014 | Wright .................. | G16H 30/20 |
| | | | | 705/2 |
| 2015/0039346 | A1* | 2/2015 | Bradshaw ............... | G06F 16/53 |
| | | | | 705/3 |
| 2015/0149444 | A1* | 5/2015 | Bolduc ............... | G06F 16/2471 |
| | | | | 707/722 |
| 2017/0048285 | A1* | 2/2017 | Pearl .................... | G06F 16/11 |
| 2018/0089370 | A1* | 3/2018 | Yu .......................... | G16H 40/67 |
| 2019/0156927 | A1* | 5/2019 | Virkar .................... | G16H 15/00 |
| 2019/0287686 | A1* | 9/2019 | Takeda ................ | G06F 21/6254 |
| 2020/0258602 | A1* | 8/2020 | Cialdea ................. | G06F 21/606 |
| 2021/0241899 | A1* | 8/2021 | Soon-Shiong ......... | G16H 40/63 |
| 2023/0126589 | A1* | 4/2023 | Pappas .................. | G16H 30/20 |
| | | | | 607/2 |

OTHER PUBLICATIONS

An International Search Report and Written Opinion of the International Searching Authority mailed on Mar. 6, 2023 in connection with PCT/US2022/047843.

* cited by examiner

| subject_id_or | cohort_name | pipeline |
|---|---|---|
| 0 | test_cohort_ADNI | "freesurfer pipe" |
| 1 | test_cohort_ADNI | "freesurfer pipe" |
| 6 | test_cohort_NACC | "ANTs.pipe" |

FIG. 6

| subject_id | cohort_name | Left_Hippocampus_volume_mm3 | Right_Hippocampus_volume_mm3 |
|---|---|---|---|
| 0 | test_cohort_ADNI | 3982 | 4299 |
| 1 | test_cohort_ADNI | 3451 | 3446 |
| 6 | test_cohort_NACC | 3312 | 3922 |

SYSTEM AND METHOD FOR GENERATING BRAIN DATA VISUALIZATIONS BASED ON FEDERATED ANALYSIS OF BRAIN DATA IN A COMPLEX COMPUTING NETWORK

CROSS-REFERENCE TO RELATED APPLICATIONS

The present application claims priority to U.S. Provisional Patent Application No. 63/272,249 filed Oct. 27, 2021 entitled "System and method for remotely processing shared data", which is incorporated herein by reference in its entirety as set forth in full.

BACKGROUND

Protected medical data have privacy policies/protocols that need to be adhered to when accessing said protected medical data. In some cases, there is a need to access certain data elements of the protected medical data without violating access rules in client-server systems. Beyond accessing the protected medical data, a need may arise for selectively conducting analysis operations on one or more elements of the protected medical data without violating the privacy policies of the protected medical data. More importantly databases and systems that manage such protected medical data are configured to enforce strict access policies for said protected medical data because the implications of not enforcing said access policies or privacy protocols may be dire. In particular, accessing protected medical data from one or more data sources for the purpose of executing analysis operations is problematic especially when such data is governed by specific and often varying privacy policies. There is a need for a platform that shields certain portions or elements of the protected medical data (e.g., brain data) while providing other elements of the protected medical data for analysis operations without violating any access protocols.

BRIEF SUMMARY

The disclosed systems and methods relate to generating brain data visualizations based on federated analysis of brain data. In exemplary embodiments, the brain data visualizations are generated using a system (e.g., a framework server discussed below) comprising a framework. The framework may include a first computing platform that comprises one or more servers. The framework may also include a first application for communicating via a communication network with a second computing platform that is different from the first computing platform. The second computing platform may comprise a database that stores protected medical data including a plurality of data elements that are directly inaccessible individually or directly inaccessible in aggregate by a user of the first computing platform. In one embodiment, the one or more servers of the first computing platform comprise memory storing instructions that are executable to execute the certain processing stages outlined in this disclosure. The instructions stored in the memory of the one or more servers may be executed by a computer processor of the first computing platform to receive workflow data for executing one or more brain analysis operations on first brain data comprised in the protected medical data of the second computing platform. The instructions may be further executed to designate an application parameter for mapping the workflow data to at least one brain analysis application that executes the one or more brain analysis operations. Furthermore, the instructions may be executed to determine an identifier for the first brain data comprised in the protected medical data of the second computing platform, such that the first brain data is associated with a set of subjects having at least one brain characteristic in common. In some embodiments, the instructions may be executed by the computer processor of the first computing platform to combine the workflow data, the parameter, and the identifier to generate a first pipeline file.

Furthermore, the instructions may be executed by the computer processor of the first computing platform to initiate generation of a first graphical user interface of the first application on a display device of a first user. In some cases, the instructions are executed to receive a first input from the first user using the first graphical user interface. The first input may include at least one of: a selection of the first pipeline file or metric data that indicate one or more brain metrics to be determined for the set of subjects having the at least one brain characteristic in common. Moreover, the instructions may be executed to generate a transform parameter (e.g., header information associated with stored protected medical data) for translating the identifier of the first brain data to enable indirect access of the first brain data for remote execution of the one or more brain analysis operations on the second computing platform. In addition, the instructions may be executed by the computer processor associated with the first computing platform to transmit the first pipeline file with the transform parameter to the second computing platform for execution of the one or more brain analysis operations on the first brain data by the second computing platform (e.g., data partner system discussed below). In response to receiving analysis data generated from executing the one or more brain analysis operations on the first brain data, the instructions may be executed by the computer processor of the first computing platform to format the analysis data to generate a brain data visualization on the display device of the first user. According to some implementations, the brain data visualization indicates the one or more brain metrics such that the one or more brain metrics characterize at least one brain condition associated with the set of subjects.

BRIEF DESCRIPTION OF THE DRAWINGS

The disclosure is illustrated by way of example, and not by way of limitation, in the figures of the accompanying drawings in which like reference numerals are used to refer to similar elements. It is emphasized that various features may not be drawn to scale and the dimensions of various features may be arbitrarily increased or reduced for clarity of discussion.

FIG. 4 shows an exemplary graphical user interface for selecting a pipeline.

FIG. 5 illustrates an exemplary data structure for transmitting a pipeline file to a data partner system for federated analysis of brain data.

FIG. 6 shows an exemplary analysis data for generating multi-dimensional visualizations.

DETAILED DESCRIPTION

The figures and descriptions provided may have been simplified to illustrate aspects that are relevant for a clear understanding of the described devices, systems, and methods, while eliminating, for the purpose of clarity, other aspects that may be found in typical similar devices, systems, and methods.

The terminology used in this disclosure is for the purpose of describing particular exemplary embodiments only and is not intended to be limiting. For example, as used, the singular forms "a", "an" and "the" may be intended to include plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The described method steps, processes, and operations are not to be construed as necessarily requiring their performance in the particular order discussed or illustrated, unless specifically identified as an order of performance. It is further appreciated that additional or alternative steps may be employed according to some implementations.

Although the terms first, second, third, etc., may be used to describe various elements, components, regions, layers and/or sections, these elements, components, regions, layers and/or sections should not be limited by these terms. These terms may be used to distinguish one element, component, region, layer or section from another element, component, region, layer or section. That is, terms such as "first," "second," and other numerical terms, when used in this disclosure, do not imply a sequence or order unless clearly indicated by the context. In addition, the term optimal and its variants (e.g., efficient, optimally, etc.) as used in this disclosure may simply indicate improving, rather than the ultimate form of 'perfection' or the like.

System Environment

Figure 1:
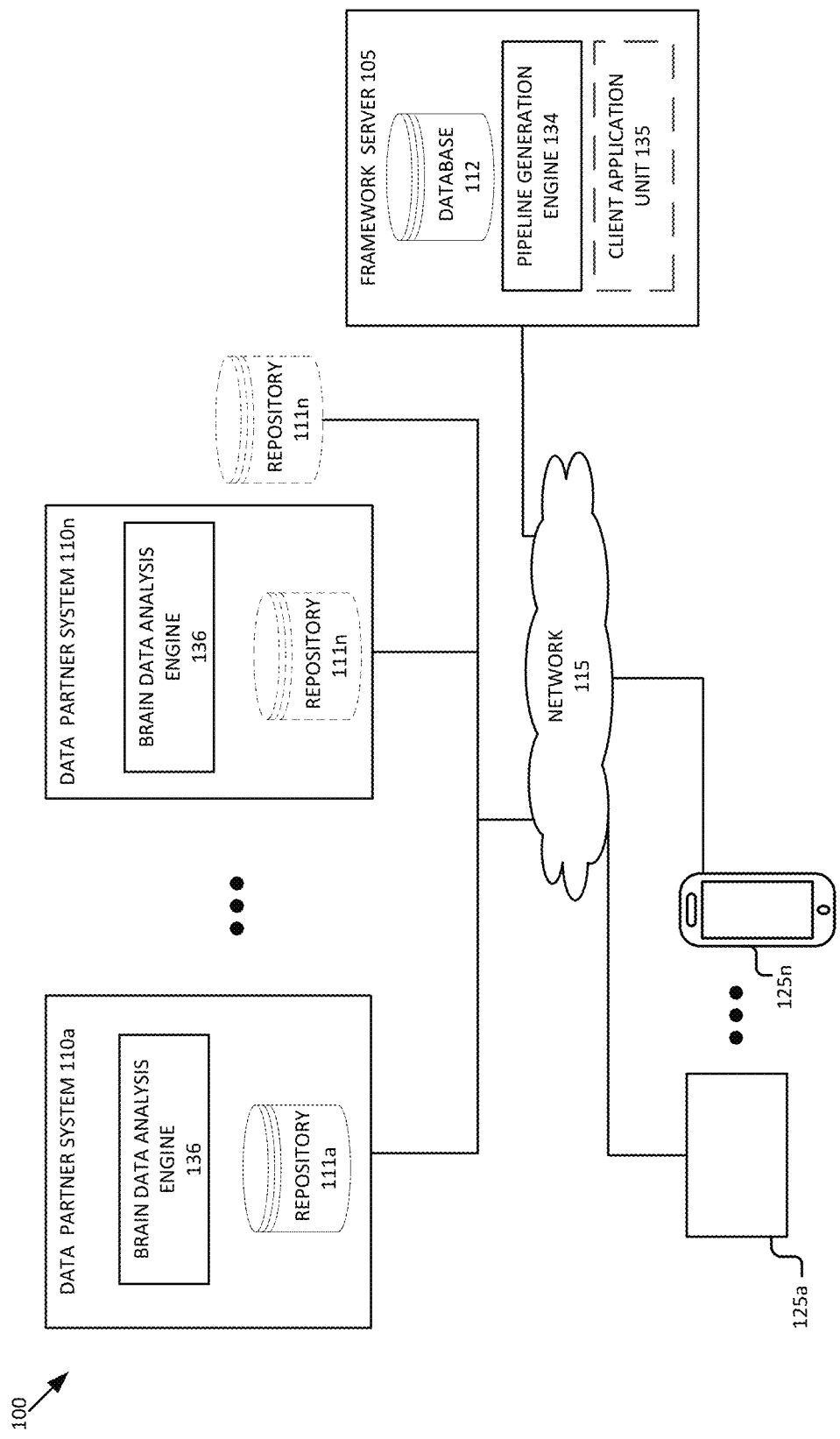
FIG. 1 shows an exemplary network system for generating brain data visualizations based on federated analysis of brain data.

Illustrated in FIG. 1 is an exemplary network system 100 for executing the principles disclosed. In the illustrated implementation, the system 100 may include a framework server 105 communicatively coupled to one or more data partner systems 110$a$, ..., 110$n$ and to one or more display devices 125$a$, ..., 125$n$ via a network 115. While a single framework server 105 is illustrated, the disclosed principles and techniques could be expanded to include multiple framework servers 105.

According to one embodiment, the framework server 105 includes a computing device such as a content server, a communication server, a laptop computer, a desktop computer, a handheld computing device, a tablet computing device, a virtual machine, a cloud-based computing solution and/or a cloud-based service, and/or the like. The framework server 105 may include a plurality of computing devices configured to communicate with one another and/or implement the techniques described herein. Further, the framework server 105 may include a database 112, a pipeline generation engine 134, and a client application unit 135. The database 112 may be configured to store user data such as user credential data as well as data generated using the pipeline generation engine 134 and/or data generated using the client application unit 135. The database 112 can be non-volatile memory or similar permanent storage device and media. For example, the one or more storage devices may include a hard disk drive, a CD-ROM device, a DVD-ROM device, a DVD-RAM device, a DVD-RW device, a flash memory device, solid state media, or some other mass storage device known in the art for storing information on a more permanent basis.

The data partner system 110$a$, ..., 110$n$ may include one or more computing systems associated with the data partner(s) discussed below. According to some implementations, the data partner systems 110$a$, ..., 110$n$ comprise a brain data analysis engine 136 and at least one database or storage repository 111. According to some implementations, the brain data analysis engine 136 may be configured to execute one or more brain analysis operations using one or more pipeline files transmitted to the data partner system 110. In some instances, the brain data analysis engine may store, for example, results from the brain analysis as well as other user data in the storage repository 111. Moreover, it is contemplated that the storage repository 111 may include a stand-alone database that is separate from, or redundant to the storage database (e.g., storage repository 111$n$) of the data partner system 110 for data backup operations associated with the data partner system 110. In addition, the storage repositories 111$a$, ..., 111$n$ may include non-volatile memory or similar permanent storage device and media. For example, the storage repositories 111$a$, ..., 111$n$ can be a hard disk drive, a CD-ROM device, a DVD-ROM device, a DVD-RAM device, a DVD-RW device, a flash memory device, solid state media, or some other mass storage device known in the art for storing information on a more permanent basis.

The network 115 may include a plurality of networks. For instance, the network 115 may include any wired and/or wireless communication network that facilitates communication between the framework server 105, the data partner systems 110$a$, ..., 110$n$, and the display devices 125$a$, ..., 125$n$. The network 115, in some instances, may include an Ethernet network, a cellular network, a computer network, the Internet, a wireless fidelity (Wi-Fi) network, a light fidelity (Li-Fi) network, a Bluetooth network, a radio frequency identification (RFID) network, a near-field communication (NFC) network, a laser-based network, and/or the like.

Turning back to FIG. 1, the display devices 125$a$, ..., 125$n$ may be handheld computing devices, smart phones, tablets, phablets, laptop computers, desktop computers, personal digital assistants (PDAs), smart devices, wearable electronic devices, biometric devices, computer servers, virtual servers, virtual machines, and/or communication servers. In some embodiments, the display devices 125$a$, ..., 125$n$ may include a plurality of computing devices configured to communicate with one another and/or implement the techniques described in this disclosure. It is appreciated that according to some implementations, visualizations associated with executing brain analysis operations may be generated on one or more display devices 125$a$, ..., 125$n$ for viewing by a user. These and other aspects are further discussed below.

Figure 2:
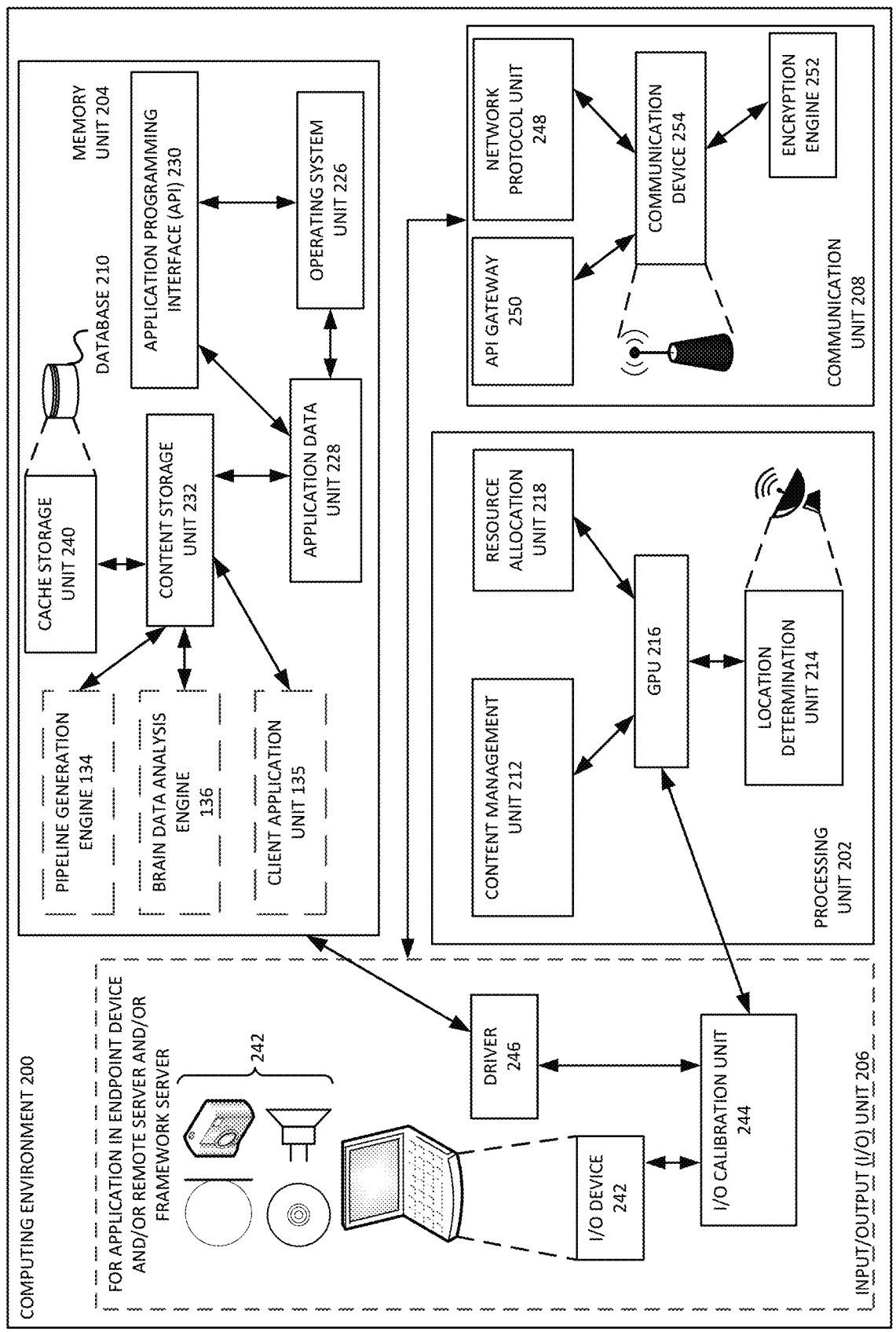
FIG. 2 illustrates a functional block diagram of a computing environment for generating brain data visualizations based on federated analysis of brain data.

FIG. 2 illustrates a functional system diagram of a computing environment 200 which can be used to implement the framework server 105, the data partner system 110, or the display device 125. The computing environment 200 and any units and/or subunits of FIG. 2 may be included in one or more elements of the system 100 as described in association with FIG. 1. The computing environment 200 may include a processing unit 202, a memory unit 204, an I/O unit 206, and a communication unit 208. The processing unit 202, the memory unit 204, the I/O unit 206, and the communication unit 208 may include one or more subunits for performing operations described in this disclosure. Additionally, each unit and/or subunit may be operatively and/or otherwise communicatively coupled with each other and to the network 110. The computing environment 200 may be implemented on general-purpose hardware and/or specifically-purposed hardware as the case may be.

The processing unit 202 may control one or more of the memory unit(s) 204, the I/O unit 206, and the communication unit 208 of the computing environment 200, as well as any included subunits, elements, components, devices, and/or functions performed by the memory unit 204, I/O unit 206, and the communication unit 208. The described sub-elements of the computing environment 200 may also be included in similar fashion in any of the other units and/or devices included in the system 100 of FIG. 1. Additionally, any actions described as being performed by a processor may be taken by the processing unit 202 of FIG. 2 alone and/or by the processing unit 202 in conjunction with one or more additional processors, units, subunits, elements, components, devices, and/or the like. Further, while one processing unit 202 may be shown in FIG. 2, multiple processing units may be present and/or otherwise included in the computing environment 200 or elsewhere in the overall system (e.g., system 100 of FIG. 1). Thus, while instructions may be described as being executed by the processing unit 202 (and/or various subunits of the processing unit 202), the instructions may be executed simultaneously, serially, and/or otherwise by one or multiple processing units 202 on one or more devices.

In some embodiments, the processing unit 202 may be implemented as one or more computer processing unit (CPU) chips and/or graphical processing unit (GPU) chips and may include a hardware device capable of executing computer instructions. The processing unit 202 may execute instructions, codes, computer programs, and/or scripts. The instructions, codes, computer programs, and/or scripts may be received from and/or stored in the memory unit 204, the I/O unit 206, the communication unit 208, subunits, and/or elements of the aforementioned units, other devices, and/or computing environments, and/or the like.

In some embodiments, the processing unit 202 may include, among other elements, subunits such as a content management unit 212, a location determination unit 214, a graphical processing unit (GPU) 216, and a resource allocation unit 218. Each of the aforementioned subunits of the processing unit 202 may be communicatively and/or otherwise operably coupled with each other.

The content management unit 212 may facilitate generation, modification, analysis, transmission, and/or presentation of content. Content may be file content, pipeline file content, brain image data content, media content, or any combination thereof. In some instances, content on which the content management unit 212 may operate includes device information, user interface data, images, text, themes, audio files, video files, documents, and/or the like. Additionally, the content management unit 212 may control (e.g., format) the audio-visual environment and/or appearance of application data during execution of various processes. In some embodiments, the content management unit 212 may interface with a third-party content server and/or memory location for execution of its operations.

The location determination unit 214 may facilitate detection, generation, modification, analysis, transmission, and/or presentation of location information. Location information may include global positioning system (GPS) coordinates, an Internet protocol (IP) address, a media access control (MAC) address, geolocation information, a port number, a server number, a proxy name and/or number, device information (e.g., a serial number), an address, a zip code, and/or the like. In some embodiments, the location determination unit 214 may include various sensors, radar, and/or other specifically-purposed hardware elements for the location determination unit 214 to acquire, measure, and/or otherwise transform location information.

The GPU 216 may facilitate generation, modification, analysis, processing, transmission, and/or presentation of content described above, as well as any data such as pipeline data or analysis data or other output data generated using at least a pipeline file and/or the like. In some embodiments, the GPU 216 may be used to render content for presentation on a computing device via, for example, a graphical display device or a graphical user interface (GUI) of the display device 125. The GPU 216 may also include multiple GPUs and therefore may be configured to perform and/or execute multiple processes in parallel.

The resource allocation unit 218 may facilitate the determination, monitoring, analysis, and/or allocation of computing resources throughout the computing environment 200 and/or other computing environments. For example, the computing environment may facilitate a high volume of data (e.g., pipeline files, brain image data, brain analysis data, etc.) to be processed and analyzed. As such, computing resources of the computing environment 200 used by the processing unit 202, the memory unit 204, the I/O unit 206, and/or the communication unit 208 (and/or any subunit of the aforementioned units) such as processing power, data storage space, network bandwidth, and/or the like may be in high demand at various times during operation. Accordingly, the resource allocation unit 218 may include sensors and/or other specially-purposed hardware for monitoring performance of each unit and/or subunit of the computing environment 200, as well as hardware for responding to the computing resource needs of each unit and/or subunit. In some embodiments, the resource allocation unit 218 may use computing resources of a second computing environment separate and distinct from the computing environment 200 to facilitate a desired operation. For example, the resource allocation unit 218 may determine a number of simultaneous computing processes and/or requests (e.g., requests associated with brain analysis operations). The resource allocation unit 218 may also determine that the number of simultaneous computing processes and/or requests meet and/or exceed a predetermined threshold value. Based on this determination, the resource allocation unit 218 may determine an amount of additional computing resources (e.g., processing power, storage space of a particular non-transitory computer-readable memory medium, network bandwidth, and/or the like) required by the processing unit 202, the memory unit 204, the I/O unit 206, the communication unit 208, and/or any subunit of the aforementioned units for safe and efficient operation of the computing environment while supporting the number of simultaneous computing processes and/or requests. The resource allocation unit 218 may then retrieve, transmit, control, allocate, and/or otherwise distribute determined amount(s) of computing resources to each element (e.g., unit and/or subunit) of the computing environment 200 and/or another computing environment.

The memory unit 204 may be used for storing, recalling, receiving, transmitting, and/or accessing various files and/or data (e.g., pipeline files, brain image data, brain analysis data, and/or the like) during operations of the computing environment 200. In some embodiments, the memory unit 204 may store instructions, code, and/or data that may be executed by the processing unit 202. For instance, the memory unit 204 may store code that execute operations associated with one or more units and/or one or more subunits of the computing environment 200. For example, the memory unit may store code for the processing unit 202, the I/O unit 206, the communication unit 208, and for itself. Moreover, the memory unit may store code for implementing the pipeline generation engine 134 associated with the framework server 105, the client application unit 135 associated with framework server 105, and the brain data analysis engine 136 associated with the data partner systems 110a, . . . , 110n.

The memory unit 204 may include various types of data storage media such as solid state storage media, hard disk storage media, virtual storage media, and/or the like. Memory unit 204 may include dedicated hardware elements such as hard drives and/or servers, as well as software elements such as cloud-based storage drives. In some implementations, memory unit 204 may include a random access memory (RAM) device, a dynamic random access memory (DRAM) device, a static random access memory (SRAM) device, flash memory, read only memory (ROM) device, and/or various forms of secondary storage. The RAM device may be used to store volatile data and/or to store instructions that may be executed by the processing unit 202. For example, the instructions stored by the RAM device may be a command, a current operating state of computing environment 200, an intended operating state of computing environment 200, and/or the like. As a further example, data stored in the RAM device of memory unit 204 may include instructions related to various methods and/or functionalities described in this disclosure. The ROM device may be a non-volatile memory device that may have a smaller memory capacity than the memory capacity of a secondary storage. The ROM device may be used to store instructions and/or data that may be read during execution of computer instructions. In some embodiments, access to both the RAM device and ROM device may be faster to access than the secondary storage.

Secondary storage may comprise one or more disk drives and/or tape drives and may be used for non-volatile storage of data or as an over-flow data storage device if the RAM device is not large enough to hold all working data. Secondary storage may be used to store programs that may be loaded into the RAM device when such programs are selected for execution. In some embodiments, the memory unit 204 includes one or more databases 210 for storing any data described herein. For example, depending on the implementation, the one or more databases 210 may be used as the storage repository 111 or the data partner system 110 or the database 112 of the framework server 105. In some embodiments, the memory unit 204 and/or its subunits may be local relative to the framework server 105 and/or the data partner system 110 and/or remotely located relative to the framework server 105 and/or to the data partner system 110.

Turning back to FIG. 2, the memory unit 204 may include subunits such as an operating system unit 226, an application data unit 228, an application programming interface (API) unit 230, a content storage unit 232, and a cache storage unit 240. Each of the aforementioned subunits of the memory unit 204 may be communicatively and/or otherwise operably coupled with each other and other units and/or subunits of the computing environment 200. It is also noted that the memory unit 204 may include other modules, instructions, or code that facilitate the execution of the techniques described. For instance, the memory unit 204 may include one or more modules such as pipeline generation engine 134, or a client application unit 135, or a brain data analysis engine 136, which are further discussed below.

The operating system unit 226 may facilitate deployment, storage, access, execution, and/or utilization of an operating system used by computing environment 200 and/or any other computing environment described in this disclosure. In some embodiments, operating system unit 226 may include various hardware and/or software elements that serve as a structural platform for the processing unit 202 to execute various operations described herein. Operating system unit 226 may further store various pieces of information and/or data associated with the operation of the operating system and/or computing environment 200 as a whole, such as a status of computing resources (e.g., processing power, memory availability, resource utilization, and/or the like), runtime information, modules to direct execution of operations described herein, user permissions, security credentials, and/or the like.

The application data unit 228 may facilitate deployment, storage, access, execution, and/or utilization of an application used by computing environment 200 and/or any other computing environment described herein. For example, the display device 125 may be required to download, install, access, and/or otherwise use a software application (e.g., web application such as an application associated with the framework server 105) to facilitate performance of brain analysis operations and/or generation of brain analysis data. As such, application data unit 228 may store any information and/or data associated with an application. Application data unit 228 may further store various pieces of information and/or data associated with the operation of an application and/or computing environment 200 as a whole, such as a status of computing resources (e.g., processing power, memory availability, resource utilization, and/or the like), runtime information, user interfaces, modules to direct execution of operations described herein, user permissions, security credentials, and/or the like.

The API unit 230 may facilitate deployment, storage, access, execution, and/or use of information associated with APIs of computing environment 200 and/or any other computing environment described in this disclosure. For example, computing environment 200 may include one or more APIs for various devices, applications, units, subunits, elements, and/or other computing environments to communicate with each other and/or use the same data. Accordingly, API unit 230 may include API databases containing information that may be accessed and/or used by applications, units, subunits, elements, and/or operating systems of other devices and/or computing environments. In some embodiments, each API database may be associated with a customized physical circuit included in memory unit 204 and/or API unit 230. Additionally, each API database may be public and/or private, and so authentication credentials may be required to access information in an API database. In some embodiments, the API unit 230 may enable the framework server 105 and/or the display device 125 and/or the data partner system 110 to communicate with each other.

The content storage unit 232 may facilitate deployment, storage, access, and/or utilization of information associated with performance of brain data analysis operations and/or framework processes by computing environment 200 and/or any other computing environment described. In some embodiments, content storage unit 232 may communicate with content management unit 212 to receive and/or transmit content files (e.g., media content, brain image data, brain analysis visualization data, etc.).

The cache storage unit 240 may facilitate short-term deployment, storage, access, analysis, and/or use of data. In some embodiments, cache storage unit 240 may serve as a short-term storage location for data so that the data stored in cache storage unit 240 may be accessed quickly. In some instances, cache storage unit 240 may include RAM devices and/or other storage media types for quick recall of stored data. Cache storage unit 240 may include a partitioned portion of storage media included in memory unit 204.

The I/O unit 206 may include hardware and/or software elements for the computing environment 200 to receive, transmit, and/or present information useful for performing brain analysis operation and generation of brain analysis visualizations and/or other processes as described herein. For example, elements of the I/O unit 206 may be used to receive input (e.g., first user input discussed below) from a user of the display device 125. As described, I/O unit 206 may include subunits such as an I/O device 242, an I/O calibration unit 244, and/or driver 246.

The I/O device 242 may facilitate the receipt, transmission, processing, presentation, display, input, and/or output of information as a result of executed processes described in this disclosure. In some embodiments, the I/O device 242 may include a plurality of I/O devices. In some embodiments, I/O device 242 may include a variety of elements that enable a user to interface with computing environment 200. For example, I/O device 242 may include a keyboard, a touchscreen, a button, a sensor, a biometric scanner, a laser, a microphone, a camera, and/or another element for receiving and/or collecting input from a user. Additionally and/or alternatively, I/O device 242 may include a display, a screen, a sensor, a vibration mechanism, a light emitting diode (LED), a speaker, a radio frequency identification (RFID) scanner, and/or another element for presenting and/or otherwise outputting data to a user. In some embodiments, the I/O device 242 may communicate with one or more elements of processing unit 202 and/or memory unit 204 to execute operations associated with brain data analysis and generation of visualizations associated with the brain data analysis operations for display on the display devices 125a, . . . , 125n.

The I/O calibration unit 244 may facilitate the calibration of the I/O device 242. For example, I/O calibration unit 244 may detect and/or determine one or more settings of I/O device 242, and then adjust and/or modify settings and/or optimize viewing of a graphical user interface and/or one or more visualizations associated with brain data analysis so that the I/O device 242 may operate more efficiently. According to some embodiments, the I/O calibration unit 244 may be used to format brain analysis data by resolving the analysis data into multi-dimensional components of a brain data visualization and rendering a multi-dimensional image on the display device 125 for viewing by a first user.

In some embodiments, the I/O calibration unit 244 may use a driver 246 (or multiple drivers) to calibrate I/O device 242. For example, driver 246 may include software that is installed by I/O calibration unit 244 so that an element of computing environment 200 (or an element of another computing environment) may recognize and/or integrate with I/O device 242 for disclosed processes.

The communication unit 208 may facilitate establishment, maintenance, monitoring, and/or termination of communications between computing environment 200 and other computing environments, third party server systems, and/or the like (e.g., between the framework server 105 and the display device 125 or between the framework server 105 and the data partner system 110). Communication unit 208 may also facilitate internal communications between various elements (e.g., units and/or subunits) of computing environment 200. In some embodiments, communication unit 208 may include a network protocol unit 248, an API gateway 250, an encryption engine 252, and/or a communication device 254. Communication unit 208 may include hardware and/or software elements.

The network protocol unit 248 may facilitate establishment, maintenance, and/or termination of a communication connection for computing environment 200 by way of a network. For example, the network protocol unit 248 may detect and/or define a communication protocol required by a particular network and/or network type. Communication protocols used by the network protocol unit 248 may include Wi-Fi protocols, Li-Fi protocols, cellular data network protocols, Bluetooth® protocols, WiMAX protocols, Ethernet protocols, powerline communication (PLC) protocols, and/or the like. In some embodiments, facilitation of communication for computing environment 200 may include transforming and/or translating data from being compatible with a first communication protocol to being compatible with a second communication protocol. In some embodiments, network protocol unit 248 may determine and/or monitor an amount of data traffic to consequently determine which particular network protocol is to be used for establishing a secure communication connection, transmitting data, and/or performing brain data analysis operations and/or data visualization operations and/or other processes provided in this disclosure.

The API gateway 250 may allow other devices and/or computing environments to access API unit 230 of memory unit 204 of computing environment 200. For example, a display device 125 may access API unit 230 of computing environment 200 via API gateway 250. In some embodiments, API gateway 250 may be required to validate user credentials associated with a user of a display device prior to providing access to API unit 230 to a user. API gateway 250 may include instructions for computing environment 200 to communicate with another device and/or between elements of the computing environment 200.

The encryption engine 252 may facilitate translation, encryption, encoding, decryption, and/or decoding of information received, transmitted, and/or stored by the computing environment 200. Using encryption engine 252, each transmission of data may be encrypted, encoded, and/or translated for security reasons, and any received data may be encrypted, encoded, and/or translated prior to its processing and/or storage. In some embodiments, encryption engine 252 may generate an encryption key, an encoding key, a translation key, and/or the like, which may be transmitted along with any data content.

The communication device 254 may include a variety of hardware and/or software specifically purposed to facilitate communication for computing environment 200. In some embodiments, communication device 254 may include one or more radio transceivers, chips, analog front end (AFE) units, antennas, processing units, memory, other logic, and/or other components to implement communication protocols (wired or wireless) and related functionality for facilitating communication for computing environment 200. Additionally and/or alternatively, communication device 254 may include a modem, a modem bank, an Ethernet device such as a router or switch, a universal serial bus (USB) interface device, a serial interface, a token ring device, a fiber distributed data interface (FDDI) device, a wireless local area network (WLAN) device and/or device component, a radio transceiver device such as code division multiple access (CDMA) device, a global system for mobile communications (GSM) radio transceiver device, a universal mobile telecommunications system (UMTS) radio transceiver device, a long term evolution (LTE) radio transceiver device, a worldwide interoperability for microwave access (WiMAX) device, and/or another device used for communication purposes.

Embodiments

This disclosure describes a framework that securely allows users to share or otherwise indirectly access protected sets of medical data from one or more data partner systems. The indirectly accessed medical data may include sets of stored brain data that is processed to generate brain analysis data. In particular, the framework accommodates remote computing requests or operations on brain imaging data indicating a brain condition (e.g., Alzheimer's-related data, Parkinson's Disease data, Huntington's Disease data, Dementia data, Pick's Disease data, etc.). According to one implementation, computing operations including the analysis operations on the brain data are executed in a federated manner that respects or considers or obeys data privacy protocols of repositories of data partner systems 110 to protect data being accessed on the data partner system 110.

According to some embodiments, the brain analysis operations are executed in a federated manner such that the brain analysis operations associated with a first data partner or a second data partner comprise distinct brain analysis operations because the first data partner system may have a first set of data privacy protocols and the second data partner system may have a second set of data privacy protocols. According to one embodiment, the first set of data privacy protocols may be different from the second set of data privacy protocols. In other embodiments, the first set of data privacy protocols is similar to the second set of data privacy protocols. It is appreciated that the data privacy protocols discussed in association with the first data partner and/or the second data partner include rules data that govern access of data on a data partner system. The federated architecture described above may allow interrogating protected medical data (e.g., brain data) or extracting derived metrics from protected medical data without needing to take possession of, or directly access the protected medical data because of the data privacy protocols of a data partner system. Moreover, the protected medical data on the data partner system(s) may include a plurality of data elements that are directly inaccessible individually or directly inaccessible in aggregate by a user of the framework. These aspects are further discussed below.

In some embodiments, the data partner system (e.g., data partner system 110) includes a central server that communicates with multiple client applications such as client applications associated with the framework server 105 and which are rendered on the display device 125 that are installed on the data partner system(s). According to some implementations, a plurality of brain imaging software may be installed on the data partner systems that execute remote computing operations or remote analysis of protected medical data. Furthermore, the plurality of brain imaging software and/or other medical-related software may be installed on cloud computing systems that are communicatively coupled to the data partner system(s) for access by the data partner systems and/or by a display device of a user and/or by the framework server 105. The brain imaging software may include brain imaging tools that can execute volumetric analysis operations on brain data, image registration operations on brain data, etc. These tools may be grouped using a software pipeline that may aggregate commands from different brain imaging tools and allow the construction of plurality of image processing pipelines based on one or more pipeline files.

Figure 3:
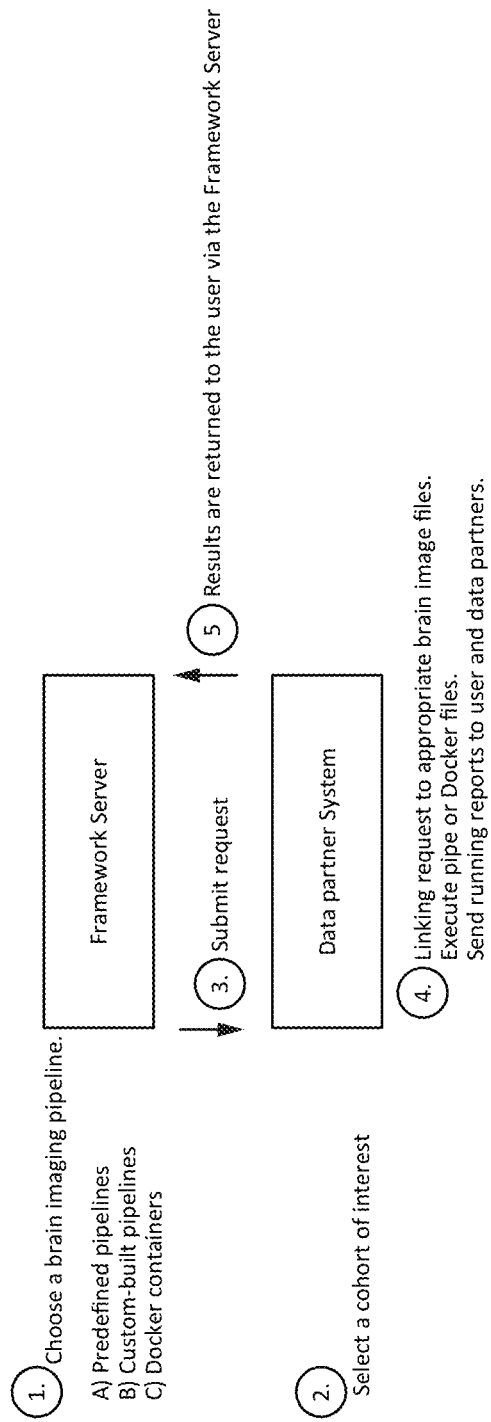
FIG. 3 depicts a high-level workflow of a framework for generating brain data visualizations based on federated analysis of brain data.

FIG. 3 depicts a high-level workflow of a framework for generating brain data visualizations based on federated analysis of brain data. According to one implementation, the client application unit 135 of FIG. 1 may initiate generation of a graphical user interface that provides display elements which receive credential data from a user before access is provided to the platform of the framework server 105. The platform of the framework server 105 provides a user with options to generate and/or create pipeline files that may be transmitted to the data partner system 110 for execution of one or more brain analysis operations. The platform of the framework server 105 may also facilitate generation of one or more data visualizations that may be generated on a display device 125.

According to some embodiments, a brain analysis request using the platform of the framework server 105 may include the following processes as shown in FIG. 3: 1. First, a selection of a pipeline (e.g., a brain imaging pipeline) may be made by a user using a graphical user interface of the platform of the framework server 105. According to some embodiments, the pipeline encapsulates analysis operations (e.g., brain data analysis operations) such that the pipeline can be distributed to one or more data partner systems and/or be used for automated processing of protected medical data (e.g., brain data) stored on one or more data partner systems 110. The available pipelines may be selected from a predefined dropdown list. For each choice, a pipeline (.pipe) file may be automatically constructed or the user may choose to upload their own custom pipelines using user-specific pipeline files. The user may also choose to upload a container file for OS-level virtualization to deliver software associated with the pipeline in packages that allow, for example, multiple files (e.g., text files, scripts, etc.) associated with commands for different pipe files to be executed on the data partner system(s) 110. In one embodiment, the pipeline file comprises a containerized application that includes a Docker container, a Singularity container, or some other container object for deploying the pipeline for execution on the data partner system(s) 110. It is appreciated that the containerized object (e.g., Docker container, Singularity container, etc.) may also be pre-approved by the data partner system(s) 110 to ensure that processing requirements including data privacy protocols of the data partner system(s) are satisfied. In some embodiments, the format of the pipeline file may be based on a pipeline infrastructure of the framework server 105 such that users can define their own custom pipelines (e.g., brain imaging processing) using a user-friendly graphical interface of the framework server 105. In some cases, the pipeline file may include different brain software that needs to run alongside useful metadata for determining a computing request comprised in the pipeline file. The pipeline file may further include information about which software to run, a username and email of a user, an identifier or name of the request comprised in the pipeline file, a format of the input data (for example, T1 weighted anatomical brain images), and a name or identifier of an output directory for storing analysis data and/or visualizations associated with brain analysis operations executed using the pipeline file.

Figure 4:
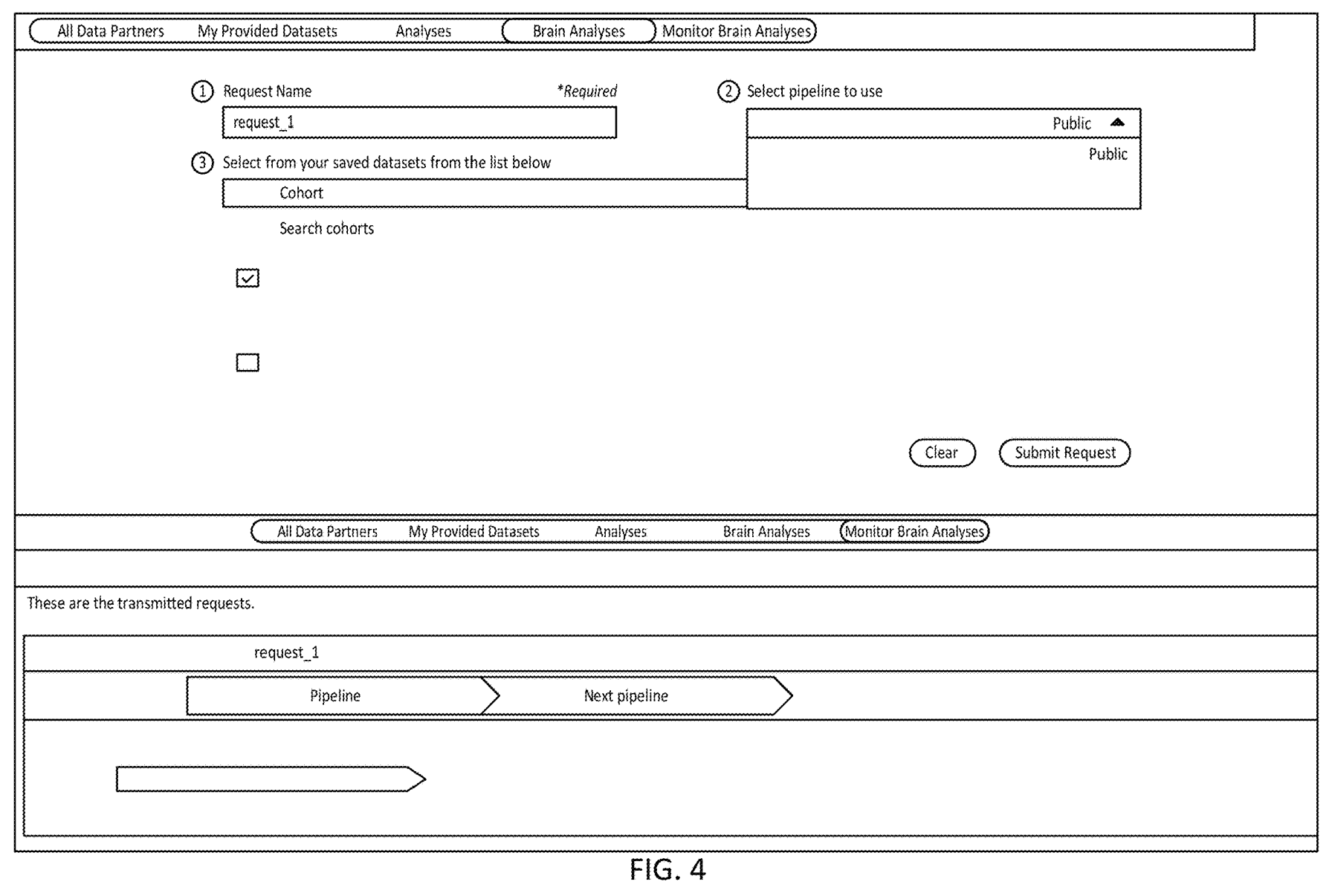

At step 2. of FIG. 3, the user may select a cohort(s) of interest for a selected pipeline. According to one embodiment, the cohort(s) of interest includes a set of subjects associated with a brain analysis study or a brain evaluation study that share certain characteristics in common as further discussed below in conjunction with FIG. 8. It is appreciated that computing requests comprised in the pipeline file may be instantiated for any user-defined cohort and may be created using the platform of the framework server 105. This, according to some embodiments, allows users to relate brain variables to cohort attributes. An exemplary graphical interface for selecting a pipeline with attendant cohort(s) of interest is provided in FIG. 4.

At step 3. of FIG. 3, the pipeline file including the request for one or more brain analysis operations may be transmitted via a communication network to a data partner system 110. In one embodiment, transmitting the pipeline file to the data partner system 110 may include transmitting a data packet including a collection of entries, for example comma-separated value (CSV) entries, Javascript object notation (JSON) entries, or any other suitable packet file format entries. For example, the data packet may include a data structure (e.g., tabular data structure) with entry sections (e.g., rows) which correspond to one or more parameters associated with the selected cohort. The one or more entry sections may indicate: i.) a subject id; ii.) a selected cohort; and iii.) required software commands for executing the request on the data partner system location. The platform of the framework server 105 may transmit the data packet via a web socket to the data partner system 110. An exemplary data structure for transmitting a pipeline file to a data partner system for federated analysis of brain data is shown in FIG. 5.

At step 4., the data packet may be parsed by the data partner system 110. According to one embodiment, the framework server 105 may facilitate transforming, translating, or mapping one or more identifiers (e.g., subject IDs) comprised in the data packet to the data partners' internal identifiers (e.g., internal subject IDs) of the data partner system 110 receiving the data packet. According to some embodiments, the one or more identifiers may comprise data associated with header information of brain imaging data stored on the data partner system. Thus, after translating the one or more headers, the data partner system 110 is able to identify specific protected medical data (e.g., brain image data) for execution of the analysis operations (e.g., brain analysis operations) on the data partner system 110. This enables the framework server 105 to maintain the data partners' data privacy protocols throughout the process of accessing specific medical data for execution of the analysis operations. In particular, a user has no means of probing the header information comprised in the identifiers within the data packet including the pipeline file transmitted to the data partner system 110. Thus, the protected medical data cannot be directly accessed without permission from the data partner system 110. In turn, the pipeline file may be processed and executed by the pipeline software on the data partner system 110 with results being generated, stored, and/or transmitted to specific storage locations based on storage location data comprised in the transmitted data packet.

In one embodiment, certain naming conventions and file type requirements may be adhered to for the analysis operations to run and for the platform of the framework server 105 to find the results. For example, if the user has T2-weighted anatomical brain images and the pipeline is defined for T1-weighted anatomical brain images, an error may be produced and electronically sent to the user (e.g., via the user's email or text message). In addition, the pipeline may be executed on the brain imaging data of a selected cohort. The platform of the framework server 105 may facilitate generation of a graphical user interface (e.g., on the display device 125) that includes a status indicator for monitoring the computing request's status (e.g., running/not running) and time elapsed. The computing request may be canceled by the user or by the data partner system 110 at any time. "Computing request" as used herein refers to the data packet including the pipeline file sent to the data partner system 110 for execution of one or more brain analysis operations. Based on an indicated output directory information comprised in the request, the data partner system 110 may check if data for the subjects and a submitted pipeline already exist. Thus, different users may not need to re-run on a given pipeline. The same can be done for embodiments with a containerized object (e.g., Docker container or Singularity container) by looking at "cached" commands associated with the containerized object. If the data partner system 110 supports grid-based computing, then the analysis operations may be distributed among different processing cores, enhancing the speed of acquisition of the results. If the pipeline uses GPU-enabled software and the data partner system has suitable hardware, then the GPU may be used to enhance the execution speed of the brain analysis operations as well. Results (e.g., analysis data) may be generated using data structures associated with a tabular file, such as comma-separated values (CSV) file as shown in FIG. 6. Each row corresponds to a different subject comprised in the cohort information. Data partner subject IDs may also be transformed back to the platform subject IDs for additional processing operations by the platform of the framework server 105. Columns of the tabular file may correspond to the output values from the analysis operations comprised in the pipeline. The framework may create an equivalent number of columns depending on how many output variables (e.g., brain variables or metrics) were calculated using the pipeline.

Figure 7:
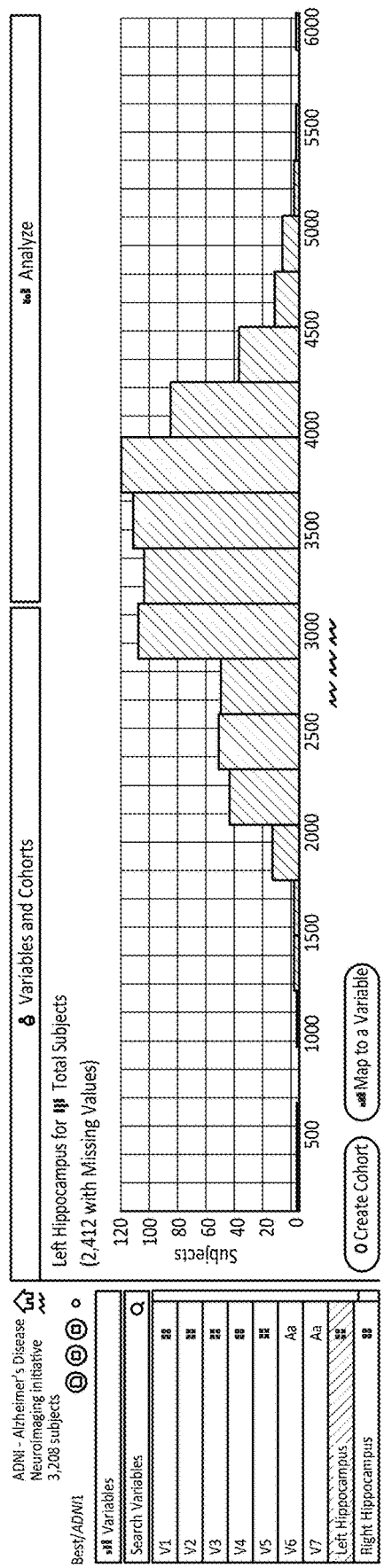
FIG. 7 depicts an exemplary multi-dimensional visualization that is generated based on analysis data.

At step 5., the analysis data or results from executing the analysis operations by the data partner system 110 may be used to generate multi-dimensional visualizations for display on one or more display devices 125 of a user. FIG. 7 depicts an exemplary multi-dimensional visualization that is generated based on analysis data. The multi-dimensional visualization may comprise a 2-dimensional visualization or a 3-dimensional visualization as the case may be. It is appreciated that the multi-dimensional visualization may indicate one or more metrics that may be constructed as a new attribute for the selected cohort. Additional analysis operations on the analysis data and/or on data associated with the multi-dimensional visualization may be further executed by the platform of the framework server 105. Such analysis may include an evaluation of the relationship between the generated analysis data and other data such as genetic data associated with the selected cohort.

Figure 8:
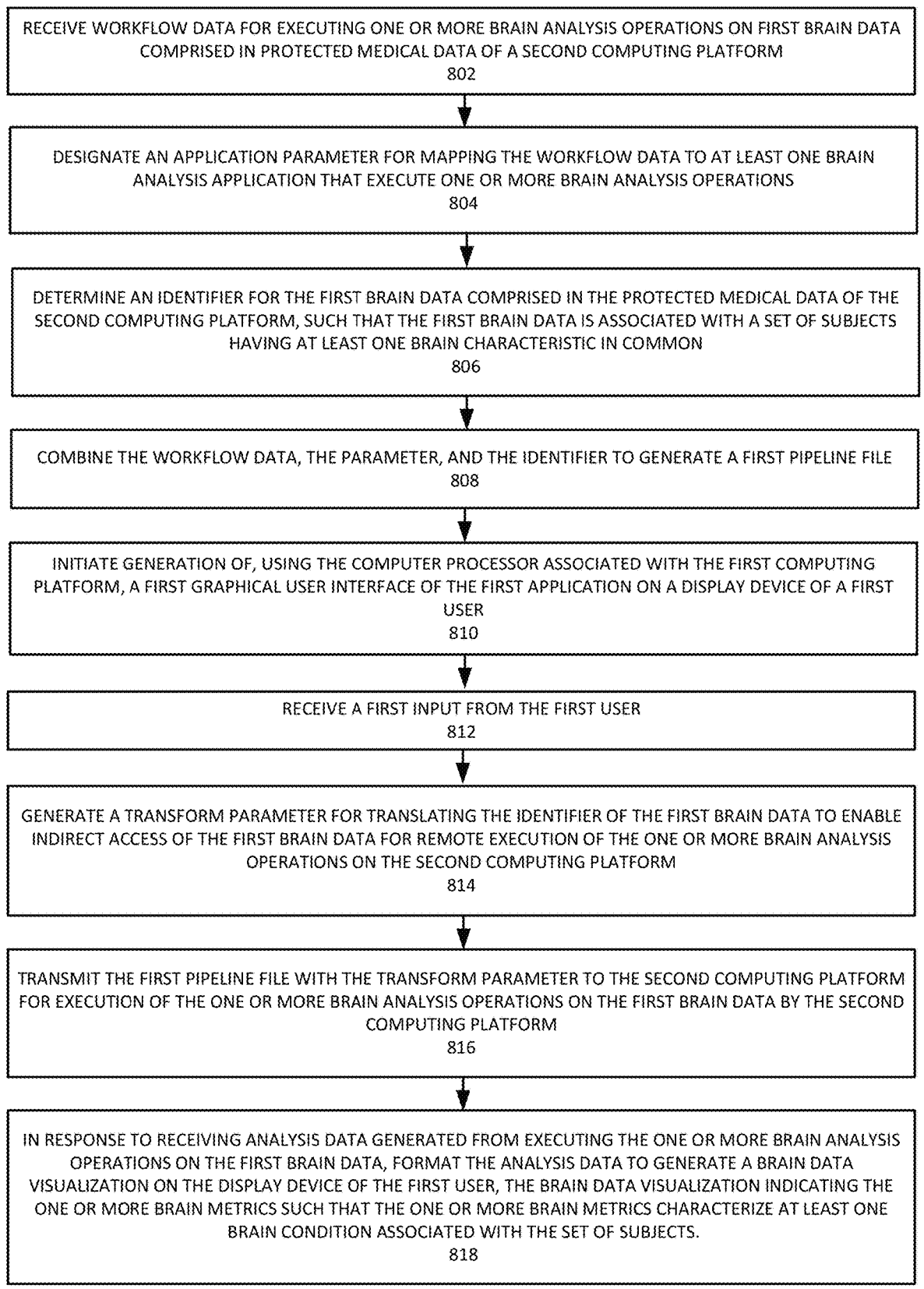
FIG. 8 shows a detailed flowchart for generating brain data visualizations based on federated analysis of brain data.

FIG. 8 shows a detailed flowchart for generating brain data visualizations based on federated analysis of brain data. In exemplary embodiments, the brain data visualizations are generated using a system (e.g., framework server 105) comprising a framework. The framework may include a first computing platform that comprises one or more servers. The framework may also include a first application for communicating via a communication network with a second computing platform that is different from the first computing platform. The second computing platform may comprise a database that stores protected medical data including a plurality of data elements that are directly inaccessible individually or directly inaccessible in aggregate by a user of the first computing platform. In one embodiment, the one or more servers of the first computing platform comprise memory storing instructions that are executable to execute the various processing stages outlined in FIG. 8.

At block 802, the instructions stored in the memory of the one or more servers may be executed by a computer processor of the first computing platform to receive, at block 802, workflow data for executing one or more brain analysis operations on first brain data comprised in the protected medical data of the second computing platform. The instructions may be further executed to designate, at block 804 an application parameter for mapping the workflow data to at least one brain analysis application that executes the one or more brain analysis operations. Furthermore, the instructions may be executed to determine, at block 806, an identifier for the first brain data comprised in the protected medical data of the second computing platform, such that the first brain data is associated with a set of subjects having at least one brain characteristic in common. In some embodiments, the instructions may be executed by the computer processor of the first computing platform to combine, at block 808, the workflow data, the parameter, and the identifier to generate a first pipeline file. Furthermore, the instructions may be executed by the computer processor of the first computing platform to initiate, at block 810 generation of a first graphical user interface of the first application on a display device of a first user.

The instructions may be further executed to receive, at block 812, a first input from the first user using the first graphical user interface. In one embodiment, the first input includes at least one of: a selection of the first pipeline file, or metric data that indicate one or more brain metrics to be determined for the set of subjects having the at least one brain characteristic in common. Moreover, the instructions may be executed to generate, at block 814, a transform parameter (e.g., header information associated with stored protected data) for translating the identifier of the first brain data to enable indirect access of the first brain data for remote execution of the one or more brain analysis operations on the second computing platform. In addition, the instructions may be executed by the computer processor associated with the first computing platform to transmit, at block 816, the first pipeline file with the transform parameter to the second computing platform for execution of the one or more brain analysis operations on the first brain data by the second computing platform (e.g., data partner system 110). In response to receiving analysis data generated from executing the one or more brain analysis operations on the first brain data, the instructions may be executed by the computer processor of the first computing platform to format, at block 818, the analysis data to generate a brain data visualization on the display device of the first user. According to some implementations, the brain data visualization indicates the one or more brain metrics such that the one or more brain metrics characterize at least one brain condition associated with the set of subjects.

These and other implementations may each optionally include one or more of the following features. The brain data visualization is used to execute a correlation operation that correlates brain features associated with the one or more brain metrics comprised in the brain data visualization with demographic data (e.g., age data, gender data, ethnicity data, etc.) associated with the set of subjects; and execute a testing research operation that determines a relationship between the brain features associated with the one or more brain metrics and the demographic data based on the correlation operation, such that the testing research operation is used to generate a clinical data report associated with the set of subjects. According to some embodiments, the clinical data report includes biostatistics data that inform brain-healthcare operations associated with a subset of the set of subjects or that inform brain-healthcare operations associated with the set of subjects. The first brain data, according to some implementations, comprises one or more of: brain imaging data associated with the set of subjects such that the brain imaging data is obtained using magnetic resonance imaging (MRI); brain imaging data associated with the set of subjects such that the brain imaging data is obtained using positron emission tomography (PET); and brain data associated with the set of subjects such that the brain data is obtained using an electrophysiological data capturing process of brain measurements of the set of subjects. Moreover, the first user may be provided access to the first brain data by the second computing platform based on first credential data of the first user associated with the first pipeline file. A second user may be denied access to the first brain data by the second computing platform based on second credential data of the second user associated with a second pipeline file. In addition, the first pipeline file may comprise a containerized application such that the containerized application includes one of a Docker container or a Singularity container.

In addition, the workflow data comprised in the first pipeline file may include the one or more brain analysis operations. The one or more brain analysis operations may include at least one of: a skull stripping operation comprising digitally isolating brain tissue from non-brain tissue using brain image data (e.g., MRI data); a bias field correction operation comprising estimating a correction field for a region comprised in the brain image data based on a series of local estimates of tissue gain variations associated with the region comprised in the brain image data; a segmentation operation comprising quantifying tissue volume and analyzing anatomical structures associated with the brain image data; operations associated with reconstructing a cortical surface or a subcortical brain structure of the brain image data; operations associated with labeling one or more regions on the cortical surface or the subcortical brain structure of the brain image data; a linear or nonlinear registration operation on the cortical surface using a stereotaxic atlas that includes a quantification of records associated with brain structures with corresponding coordinates within the brain image data; a statistical analysis operation based on group morphometry differences that assess focal differences in brain anatomy of the brain image data; and a volumetric analysis operation that correlates brain volume data with one or more mental or cognitive medical conditions. These operations, according to some embodiments, are executed on the data partner system 110 using at least one brain imaging application. Moreover, the one or more brain metrics may be based on the one or more brain analysis operations such that the one or more brain metrics include: a hippocampal volume metric; one or more segmentation statistics including volume of ventricles or volume of white matter; or a connectivity metric that determines an amount of connectivity between left and right hippocampal data associated with the brain image data.

Figure 9:
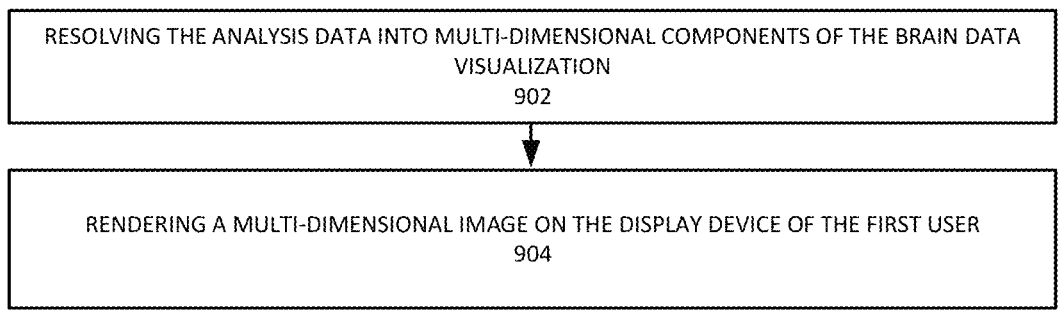
FIG. 9 shows an exemplary flowchart for formatting the analysis data.

According to some implementations, the first pipeline file comprises one of: a user-defined pipeline file generated based on pipeline customization data provided by the first user, or a system-defined pipeline file generated based on a plurality of pipeline workflow data associated with a plurality of users. In addition, the analysis data may be stored in at least one database associated with the second computing platform, and in response to the second computing platform receiving a third pipeline file similar to the first pipeline file and associated with the first brain data, the analysis data may be automatically transmitted to the first computing platform to generate the brain data visualization for rendering on a second user device of a second user. In some cases, formatting the analysis data comprises: resolving the analysis data into multi-dimensional components of the brain data visualization, and rendering a multi-dimensional image on the display device of the first user based on the multi-dimensional components as shown in the Flowchart of FIG. 9. In addition, the multi-dimensional image may be rendered on the display device of the first user based on a device type of the display device (e.g., display device 125) of the first user such that the device type comprises one of: a mobile computing device, a desktop computing device, or a tablet computing device.

According to some embodiments, the second computing platform is associated with a first data partner comprised in a plurality of data partners having a plurality of second computing platforms (e.g., computing platforms of the data partner system(s) 110), such that the plurality of second computing platforms include databases that store protected medical data including a plurality of data elements that are directly inaccessible individually or directly inaccessible in aggregate by a user of the first computing platform. Moreover, the first user input may comprise at least one of: directory data for storing the analysis data, or electronic address data for automatically transmitting the analysis data and/or generated visualizations based on the analysis data to the display device of the first user or to a display device of a second user. It is appreciated that the first user input may be included in the request or data packet sent to the data partner system 110 for execution of the analysis operations on one or more protected medical data. Furthermore, the disclosed system (e.g., framework server 105) may comprise a cloud-computing system. According to one embodiments, the analysis data generated from executing one or more analysis operations on the data partner system 110 may be electronically synthesized with a plurality of analysis data generated from one or more second computing platforms associated with a plurality of data partner systems 110 to generate synthesized brain data such that the brain data visualization is generated based on the synthesized brain data.

Furthermore, in response to transmitting the first pipeline file with the transform parameter to the second computing platform, a status indicator may be generated on the display device of the first user, such that the status indicator is dynamically updated to track a completion status of the one or more brain analysis operations being executed on the data partner system 110. Moreover, the brain analysis application may comprise a brain imaging application. Additionally, the at least one brain characteristic may comprise one or more of: age data of the set of subjects, cognitive score data based on cognitive tests conducted on the set of subjects, genetic information associated with the set of subjects, or gender information associated with the set of subjects.

As described herein, the disclosure relates to a framework that allows for remotely executing analysis operations on protected sets of medical data while ensuring data privacy protocols associated with the protected sets of medical data are observed. While the embodiments described are directed to remote computing requests for brain image data, the framework may be applicable to other applications or environments that require remote processing of information while protecting or controlling access to protected data.

Reference in the specification to "one implementation" or "an implementation" means that a particular feature, structure, or characteristic described in connection with the implementation is included in at least one implementation of the disclosure. The appearances of the phrase "in one implementation," "in some implementations," "in one instance," "in some instances," "in one case," "in some cases," "in one embodiment," or "in some embodiments" in various places in the specification are not necessarily all referring to the same implementation or embodiment.

Finally, the above descriptions of the implementations of the present disclosure have been presented for the purposes of illustration and description. It is not intended to be exhaustive or to limit the present disclosure to the precise form disclosed. Many modifications and variations are possible in light of the above teaching. It is appreciated that the scope of the present disclosure be limited not by this detailed description, but rather by the claims of this application. The present disclosure may be embodied in other specific forms without departing from the spirit or essential characteristics thereof. Accordingly, the above discussed subject-matter is illustrative, but not limiting, of the scope of the present disclosure, which is set forth in the following claims.

What is claimed is:

1. A system for generating brain data visualizations based on federated analysis of brain data, the system comprising a framework including:
   a first computing platform including one or more servers; and
   a first application for communicating via a communication network with a second computing platform that is different from the first computing platform, the second computing platform including a database that stores protected medical data including a plurality of data elements that are directly inaccessible individually or directly inaccessible in aggregate by a user of the first computing platform, wherein the one or more servers of the first computing platform comprise memory storing instructions that are executable to:
      receive, using a computer processor associated with the first computing platform, workflow data for executing one or more brain analysis operations on first brain data comprised in the protected medical data of the second computing platform;
      designate, using the computer processor associated with the first computing platform, an application parameter for mapping the workflow data to at least one brain analysis application that executes the one or more brain analysis operations;
      determine, using the computer processor associated with the first computing platform, an identifier for the first brain data comprised in the protected medical data of the second computing platform, such that the first brain data is associated with a set of subjects having at least one brain characteristic in common;
      combine, using the computer processor associated with the first computing platform, the workflow data, the parameter, and the identifier to generate a first pipeline file;
      initiate generation of, using the computer processor associated with the first computing platform, a first graphical user interface of the first application on a display device of a first user;

receive, using the computer processor and the first graphical user interface, a first input from the first user, the first input including at least one of:
a selection of the first pipeline file;
metric data that indicate one or more brain metrics to be determined for the set of subjects having the at least one brain characteristic in common;
generate, using the computer processor of the first computing platform, a transform parameter for translating the identifier of the first brain data to enable indirect access of the first brain data for remote execution of the one or more brain analysis operations on the second computing platform;
transmit, using the computer processor associated with the first framework, the first pipeline file with the transform parameter to the second computing platform for execution of the one or more brain analysis operations on the first brain data by the second computing platform; and
in response to receiving analysis data generated from executing the one or more brain analysis operations on the first brain data, format, using the computer processor associated with the first framework, the analysis data to generate a brain data visualization on the display device of the first user, the brain data visualization indicating the one or more brain metrics such that the one or more brain metrics characterize at least one brain condition associated with the set of subjects.

2. The system of claim 1, wherein the brain data visualization is used to:
execute a correlation operation that correlates brain features associated with the one or more brain metrics comprised in the brain data visualization with demographic data associated with the set of subjects, and
execute a testing research operation that determines a relationship between the brain features associated with the one or more brain metrics and the demographic data based on the correlation operation, such that the testing research operation is used to generate a clinical data report associated with the set of subjects.

3. The system of claim 1, wherein the first brain data comprises one or more of:
brain imaging data associated with the set of subjects, the brain imaging data being obtained using magnetic resonance imaging (MRI),
brain imaging data associated with the set of subjects, the brain imaging data being obtained using positron emission tomography (PET), and
brain data associated with the set of subjects, the brain data being obtained using an electrophysiological data capturing process of brain measurements of the set of subjects.

4. The system of claim 1, wherein:
the first user is provided access to the first brain data by the second computing platform based on first credential data of the first user associated with the first pipeline file, and
a second user is denied access to the first brain data by the second computing platform based on second credential data of the second user associated with a second pipeline file.

5. The system of claim 1, wherein the first pipeline file comprises a containerized application, the containerized application including one of:
a Docker container, or
a Singularity container.

6. The system of claim 1, wherein the workflow data comprised in the first pipeline file includes the one or more brain analysis operations, the one or more brain analysis operations including at least one of:
a skull stripping operation comprising digitally isolating brain tissue from non-brain tissue using brain image data (e.g., MRI data),
a bias field correction operation comprising estimating a correction field for a region comprised in the brain image data based on a series of local estimates of tissue gain variations associated with the region comprised in the brain image data,
a segmentation operation comprising quantifying tissue volume and analyzing anatomical structures associated with the brain image data,
operations associated with reconstructing a cortical surface or a subcortical brain structure of the brain image data,
operations associated with labeling one or more regions on the cortical surface or the subcortical brain structure of the brain image data,
a linear or nonlinear registration operation on the cortical surface using a stereotaxic atlas that includes a quantification of records associated with brain structures with corresponding coordinates within the brain image data,
a statistical analysis operation based on group morphometry differences that assess focal differences in brain anatomy of the brain image data, and
a volumetric analysis operation that correlates brain volume data with one or more mental or cognitive medical conditions.

7. The system of claim 6, wherein the one or more brain metrics are based on the one or more brain analysis operations, the one or more brain metrics including:
a hippocampal volume metric,
one or more segmentation statistics including volume of ventricles or volume of white matter,
a connectivity metric that determines an amount of connectivity between left and right hippocampal data associated with the brain image data.

8. The system of claim 1, wherein the first pipeline file comprises one of:
a user-defined pipeline file generated based on pipeline customization data provided by the first user, or
a system-defined pipeline file generated based on a plurality of pipeline workflow data associated with a plurality of users.

9. The system of claim 1, wherein:
the analysis data is stored in at least one database associated with the second computing platform, and
in response to the second computing platform receiving a third pipeline file similar to the first pipeline file and associated with the first brain data, automatically transmitting the analysis data to the first computing platform to generate the brain data visualization for rendering on a second user device of a second user.

10. The system of claim 1, wherein formatting the analysis data comprises:
resolving the analysis data into multi-dimensional components of the brain data visualization, and
rendering a multi-dimensional image on the display device of the first user based on the multi-dimensional components.

11. The system of claim 10, wherein the multi-dimensional image is rendered on the display device of the first user based on a device type of the display device of the first user, the device type comprising one of:
  a mobile computing device,
  a desktop computing device, or
  a tablet computing device.

12. The system of claim 1, wherein the second computing platform is associated with a first data partner comprised in a plurality of data partners having a plurality of second computing platforms, such that the plurality of second computing platforms include databases that store protected medical data including a plurality of data elements that are directly inaccessible individually or directly inaccessible in aggregate by a user of the first computing platform.

13. The system of claim 1, wherein a first user input comprises at least one of:
  directory data for storing the analysis data, or
  electronic address data for automatically transmitting the analysis data to the first user or to a second user.

14. The system of claim 1, wherein the system comprises a cloud-computing system.

15. The system of claim 1, wherein:
  the analysis data is electronically synthesized with a plurality of analysis data generated from one or more second computing platforms to generate synthesized brain data, and
  the brain data visualization is generated based on the synthesized brain data.

16. The system of claim 1, wherein in response to transmitting the first pipeline file with the transform parameter to the second computing platform, a status indicator is generated on the display device of the first user, such that the status indicator is dynamically updated to track a completion status of the one or more brain analysis operations.

17. The system of claim 1, wherein the brain analysis application comprises a brain imaging application.

18. The system of claim 1, wherein the least one brain characteristic comprises one or more of:
  age of the set of subjects,
  cognitive scores based on cognitive tests conducted on the set of subjects,
  genetic information associated with the set of subjects, or
  gender information associated with the set of subjects.

19. A method for generating brain data visualizations based on federated analysis of brain data, the method comprising:
  receiving, using a computer processor associated with a first computing platform, workflow data for executing one or more brain analysis operations on first brain data comprised in protected medical data of a second computing platform, wherein:
    the first computing platform is comprised in a framework;
    the framework comprises a first application for communicating via a communication network with the second computing platform that is different from the first computing platform, the second computing platform including a database that stores protected medical data including a plurality of data elements that are directly inaccessible individually or directly inaccessible in aggregate by a user of the first computing platform;
  designating, using the computer processor associated with the first computing platform, an application parameter for mapping the workflow data to at least one brain analysis application that executes the one or more brain analysis operations;
  determining, using the computer processor associated with the first computing platform, an identifier for the first brain data comprised in the protected medical data of the second computing platform, such that the first brain data is associated with a set of subjects having at least one brain characteristic in common;
  combining, using the computer processor associated with the first computing platform, the workflow data, the parameter, and the identifier to generate a first pipeline file;
  initiating generation of, using the computer processor associated with the first computing platform, a first graphical user interface of the first application on a display device of a first user;
  receiving, using the computer processor and the first graphical user interface, a first input from the first user, the first input including at least one of:
    a selection of the first pipeline file;
    metric data that indicate one or more brain metrics to be determined for the set of subjects having the at least one brain characteristic in common;
  generating, using the computer processor of the first computing platform, a transform parameter for translating the identifier of the first brain data to enable indirect access of the first brain data for remote execution of the one or more brain analysis operations on the second computing platform;
  transmitting, using the computer processor associated with the first framework, the first pipeline file with the transform parameter to the second computing platform for execution of the one or more brain analysis operations on the first brain data by the second computing platform; and
  in response to receiving analysis data generated from executing the one or more brain analysis operations on the first brain data, formatting, using the computer processor associated with the first framework, the analysis data to generate a brain data visualization on the display device of the first user, the brain data visualization indicating the one or more brain metrics such that the one or more brain metrics characterize at least one brain condition associated with the set of subjects.

20. A computer program comprising instructions, that when executed by a computer processor of a computing device associated with a first computing platform, causes the computing device to:
  receive workflow data for executing one or more brain analysis operations on first brain data comprised in protected medical data of a second computing platform, wherein:
    the first computing platform is comprised in a framework;
    the framework comprises a first application for communicating via a communication network with the second computing platform that is different from the first computing platform, the second computing platform including a database that stores protected medical data including a plurality of data elements that are directly inaccessible individually or directly inaccessible in aggregate by a user of the first computing platform;
  designate an application parameter for mapping the workflow data to at least one brain analysis application that executes the one or more brain analysis operations;
  determine an identifier for the first brain data comprised in the protected medical data of the second computing platform, such that the first brain data is associated with a set of subjects having at least one brain characteristic in common;

combine the workflow data, the parameter, and the identifier to generate a first pipeline file;

initiate generation of, using the computer processor associated with the first computing platform, a first graphical user interface of the first application on a display device of a first user;

receive a first input from the first user, the first input including at least one of:
  a selection of the first pipeline file;
  metric data that indicate one or more brain metrics to be determined for the set of subjects having the at least one brain characteristic in common;

generate a transform parameter for translating the identifier of the first brain data to enable indirect access of the first brain data for remote execution of the one or more brain analysis operations on the second computing platform;

transmit the first pipeline file with the transform parameter to the second computing platform for execution of the one or more brain analysis operations on the first brain data by the second computing platform; and
  in response to receiving analysis data generated from executing the one or more brain analysis operations on the first brain data, format the analysis data to generate a brain data visualization on the display device of the first user, the brain data visualization indicating the one or more brain metrics such that the one or more brain metrics characterize at least one brain condition associated with the set of subjects.

* * * * *